(12) United States Patent
Håkansson et al.

(10) Patent No.: US 8,137,952 B2
(45) Date of Patent: Mar. 20, 2012

(54) THERMOSTABLE LACTOBACILLUS STRAINS

(75) Inventors: Eva Grahn Håkansson, Umeå (SE); Jennie Ekbeck, Umeå (SE)

(73) Assignee: Probac AB (SE)

( * ) Notice: Subject to any disclaimer, the term of this patent is extended or adjusted under 35 U.S.C. 154(b) by 588 days.

(21) Appl. No.: 12/225,221

(22) PCT Filed: Mar. 14, 2007

(86) PCT No.: PCT/SE2007/050156
§ 371 (c)(1),
(2), (4) Date: Feb. 4, 2009

(87) PCT Pub. No.: WO2007/108764
PCT Pub. Date: Sep. 27, 2007

(65) Prior Publication Data
US 2009/0208606 A1   Aug. 20, 2009

(30) Foreign Application Priority Data
Mar. 17, 2006 (SE) ........................ 0600606

(51) Int. Cl.
*C12N 1/20* (2006.01)
*C12N 1/00* (2006.01)
*A23C 9/12* (2006.01)
(52) U.S. Cl. .................. 435/252.9; 435/243; 426/61
(58) Field of Classification Search .................. None
See application file for complete search history.

(56) References Cited

U.S. PATENT DOCUMENTS

| 4,110,477 | A | 8/1978 | Naruse et al. |
| 6,761,885 | B1 | 7/2004 | Håkansson et al. |

FOREIGN PATENT DOCUMENTS

| DE | 3335351 | 4/1985 |
| WO | WO-94/00019 A1 | 1/1994 |
| WO | WO-98/55131 A1 | 12/1998 |

OTHER PUBLICATIONS

"International Application Serial No. PCT/SE2007/050156, International Search Report mailed Jul. 6, 2007", 6 pgs.

*Primary Examiner* — Yong Pak
(74) *Attorney, Agent, or Firm* — Schwegman, Lundberg & Woessner, P.A.

(57) ABSTRACT

The present invention relates to the *Lactobacillus* genus that have the ability to survive in high temperature environments. These thermostable microorganisms have the ability to produce viable antibacterial agents in different food products after heat 5 treatment. The thermostable microorganisms of the *Lactobacillus* genus may be included in food products that demand high temperature. A further object of the present invention is the ability of a food product comprising the thermostable microorganisms of the *Lactobacillus* genus for promoting immunotolerance in autoimmune diseases such as coeliac disease. Furthermore, two novel strains of *lactobacillus* 10 genus are disclosed, *Lactobacillus plantarum* LB3e and *Lactobacillus plantarum* LB7c deposited at Deutsche Sammlung von Mikroorganismen und Zeelkulturen, which have been assigned accession number 17852 and 17853 respectively.

3 Claims, 6 Drawing Sheets

THERMOSTABLE LACTOBACILLUS STRAINS

RELATED APPLICATIONS

This application is a nationalization under 35 U.S.C. 371 of PCT/SE2007/050156, filed Mar. 14, 2007 and published as WO 2007/108764 A2, on Sep. 27, 2007, which claimed priority under 35 U.S.C. 119 to Sweden Patent Application Serial No. 0600606-8, filed Mar. 17, 2006; which applications and publication are incorporated herein by reference and made a part hereof.

TECHNICAL FIELD

The present invention relates to the *Lactobacillus* genus that has the ability to survive in high temperature environments. These thermostable microorganisms have the ability to produce viable antibacterial agents in different food products after heat treatment. The thermostable microorganisms of the *Lactobacillus* genus may be included in food products that demand high temperature. A further object of the present invention is the ability of a food product comprising the thermostable microorganisms of the *Lactobacillus* genus to promote immunotolerance and homeostasis. Furthermore, two novel strains of *Lactobacillus* genus are disclosed.

BACKGROUND OF THE INVENTION

Probiotics are defined as "live microorganisms administered in adequate amounts which confer a beneficial health effect on the host". Most probiotics are bacteria, which are small, single-celled organisms of the genera *Lactobacillus, Lactococcus* or *Bifidobacterium*.

At a minimum, probiotic products should be safe, effective, and should maintain their effectiveness and potency until they are consumed. This requires a responsible approach both by the producer and the consumer.

At birth *Lactobacillus* strains together with *Bifidobacteria* and *Lactococcus* are the first to colonise the sterile intestines. In adults *Lactobacillus* strains are also the dominating normal flora in the intestine. It has been known that it is beneficial to include lactic acid producing bacteria such as *Lactobacillus* in the diet. Today a lot of the products that have included lactic acid bacteria are administered in dairy products or are administered in the form of concentrates of the microorganisms, in the form of suitably formulated preparations including powders, granulates tablets or capsules containing a high number of one or more species of the beneficial microorganisms. A lot of these applications include protein or sugar from milk, against which many people are intolerant or allergic. It is advantageous to administer the beneficial microorganisms as a part of the normal diet. Therefore, it is desirable to incorporate the beneficial microorganisms in types of food products which are consumed universally and regularly in considerable quantities by a majority of consumers such as bread or other cereal products. However, several food products are subjected to temperatures which often kill the microorganisms in the food product before they reach the consumer.

People suffering from coeliac disease (CD) are not able to eat a diet containing the protein gluten which is often represented in bread and cereal products. Further, commercially available gluten-free food products such as pasta are of a low sensory and cooking quality and usually much more expensive than normal pasta. Thus, there is a need to provide new and less expensive food products such as pasta, bread and cereal products that can be consumed by people suffering from coeliac disease.

WO 94/00019 relates to baked products containing desirable viable microorganisms. It is concluded that microorganisms such as lactic acid bacteria are killed during the baking step as a result of heat inactivation. Accordingly, a fresh baked product does not contain any viable microorganisms at all. Therefore, a method is disclosed wherein a suspension of viable microorganisms is injected into the baked product. It is an essential feature that the bakery product is cooled down to a temperature below +70° C. before the viable microorganisms are injected. There are several problems when injecting a suspension of viable microorganisms with a high concentration into a baked product. The injected microorganisms do not show any significant growth in the bread. It is difficult to achieve an equal distribution in the baked bread and the taste could be affected. Further, expensive equipment is needed to inject the viable microorganism suspension and it is not likely that such a method could be used outside a large-scale manufacturing process. The expensive equipment and the high concentration of the suspension with microorganisms will often result in an expensive product.

Therefore, it is an object of the present invention to solve these problems.

SUMMARY OF THE INVENTION

The inventors of the present invention have surprisingly found that thermostable microorganisms of the *Lactobacillus* genus that are able to survive temperatures from +80° C. for more than 25 minutes or alternatively for more than 10 s in a microwave radiated environment and have the ability to produce viable antibacterial agents in different food products after such heat treatment.

Particularly, *Lactobacillus plantarum* and *Lactobacillus rhamnosus* have the ability to survive in high temperature and in microwave radiated environment and still produce an antibacterial agent that also inhibit growth of mould in food products. Further, two specific examples of known *Lactobacillus* strains are disclosed, *Lactobacillus plantarum* LB931 and *Lactobacillus rhamnosus*, LB21. Furthermore, two novel strains of *Lactobacillus* are disclosed, referred to as *Lactobacillus plantarum* LB7c and *Lactobacillus plantarum* LB3e.

The inventors have also shown that food products comprising the thermostable viable *Lactobacillus* strains chosen from the species *Lactobacillus plantarum* and *Lactobacillus rhamnosus* and particularly *Lactobacillus plantarum* LB931, *Lactobacillus rhamnosus*, LB21, *Lactobacillus plantarum* LB7c and *Lactobacillus plantarum* LB3e can reduce the immunological response in the intestine due to gluten. A food product containing such thermostable viable *Lactobacillus* strains promoting immunotolerance in autoimmune diseases such as coeliac disease.

DEFINITIONS

As disclosed herein, the term "LB" relates to bacteria of the genus *Lactobacillus*.

As disclosed herein, the term "thermostable" relates to bacteria that survive in temperatures higher than +80° C. for more than 25 minutes.

As disclosed herein, the term "lactic acid bacteria" relates to bacteria producing lactic acid, such as bacteria belonging to the genera *Lactobacillus* and *Lactococcus*.

As disclosed herein, the term "CFU" relates to colony-forming units.

As disclosed herein, the term "food products" relates to food products such as bread, dough, cereal products such as porridge, gruel, muesli, granola, powdered cereal based product, pasta, semi products such as soups, bake-off products, plain bread and stewed fruit.

As disclosed herein, the term "heat source" relates to heat sources that heat the food product such as a stove plate, oven, microwave radiated environment, microwave oven or a water bath.

A dough used herein usually contains a fluid such as milk or water, flour and yeast.

As disclosed herein, the term "a slice of bread" relates to a typical slice of bread which weighs about 15-40 g.

As disclosed herein, the term "bake-off products" relates to semi-finished products for which the baking will be completed after supply to the consumer.

As disclosed herein, the term "soluble substances" relates to organic acids, in organic acids, such as lactic acid, succinic acid, acetic acid, and propionic acid.

DETAILED DESCRIPTION OF THE INVENTION

The present invention relates to thermostable microorganisms of the *Lactobacillus* genus that are able to survive temperatures from +80° C. for more than 25 minutes.

It is also disclosed that thermostable microorganisms of the *Lactobacillus* genus are able to survive for more than 10 s in a microwave radiated environment.

It is disclosed that selected species of microorganisms of the *Lactobacillus* genus chosen from the species *Lactobacillus plantarum* and *Lactobacillus rhamnosus* have the ability to produce viable antibacterial agents in different food products after heat treatment.

Furthermore, two novel strains of *Lactobacillus* are disclosed, *Lactobacillus* strain chosen from the species *Lactobacillus plantarum* LB7c and *Lactobacillus plantarum* LB3e.

An embodiment is directed to microorganisms of the *Lactobacillus* strain chosen from the species *Lactobacillus plantarum* LB3e and *Lactobacillus plantarum* LB7c which have been deposited at Deutsche Sammlung von Mikroorganismen und Zeelkulturen, and have been assigned accession number 17852 and 17853 respectively that are able to survive temperatures from +80° C. for more than 25 minutes.

Any of the above mentioned *Lactobacillus* strains could be used in food products such as bread, dough, cereal products, porridge, gruel, muesli, granola, powdered cereal based product, pasta, semi products, soups, bake-off products, plain bread, stewed fruit.

Further, a food product such as bread, dough, cereal products, porridge, gruel, muesli, granola, powdered cereal based product, pasta, semi product, soups, bake-off products, plain bread, stewed fruit characterized in that said food product also contains a viable *Lactobacillus* strain wherein said deposited strains are able to survive temperatures from +80° C. for more than 25 minutes.

In further embodiments said deposited strains have been showed to survive temperatures from +80° C. for more than 30, 40, 50 and 60 minutes.

Further, a food product such as bread, dough, cereal products, porridge, gruel, muesli, granola, powdered cereal based product, pasta, semi product, soups, bake-off products, plain bread, stewed fruit characterized in that said food product also contains a viable *Lactobacillus* strain wherein said deposited strains are able to survive for more than 10 s in a microwave radiated environment.

A food product mentioned above wherein the viable *Lactobacillus* strain is chosen from the species *Lactobacillus plantarum* LB931 which has been deposited at Deutsche Sammlung von Mikroorganismen und Zellkulturen and has been assigned accession number DSM 11918, *Lactobacillus rhamnosus* LB21 which has been deposited at NCIMB Ltd, Ferguson Building, Craibstone Estate and has been assigned accession number NCIMB 40564, *Lactobacillus plantarum* LB3e (DSM 17852) and *Lactobacillus plantarum* LB7c (DSM 17853).

A food product mentioned above prepared by heat treatment of a food product starting material using a heat source exposing said food product to a temperature above +80° C. wherein that said food product also contains a viable *Lactobacillus* strain preferably chosen from the *Lactobacillus plantarum* LB931 (DSM11918), *Lactobacillus rhamnosus* LB21 (NCIMB 40564), *Lactobacillus plantarum* LB7c (DSM 17853) and *Lactobacillus plantarum* LB3e (DSM 17852) respectively.

Examples of two known *Lactobacillus* strains are disclosed, *Lactobacillus plantarum* LB931 and *Lactobacillus rhamnosus*, LB21.

In further embodiments the use of the known viable *Lactobacillus* strains chosen from the species *Lactobacillus plantarum* (DSM 11918), *Lactobacillus rhamnosus* LB21 (NCIMB 4056) for manufacturing a food product such bread, dough, cereal products, porridge, gruel, muesli, granola, powdered cereal based product, pasta, semi product, soups, bake-off products, plain bread, stewed fruit wherein said deposited strains are able to survive temperatures from +80° C. for more than 25 minutes are disclosed.

A food product mentioned above wherein the viable *Lactobacillus* strain is present in an amount above $1.0 \times 10^3$ CFU/g, preferably above $1.0 \times 10^4$ CFU/g and most preferably above 1.0×10⁵ CFU/g, living bacteria per gram of the food product after the heat treatment.

A further object of the present invention is the ability of a food product mentioned above wherein the thermostable viable *Lactobacillus* strain chosen from the species *Lactobacillus plantarum* and *Lactobacillus rhamnosus* reduces the immunological response in the intestine due to gluten and particularly, *Lactobacillus plantarum* LB931 (DSM11918), *Lactobacillus rhamnosus*, LB21 (NCIMB 40564), *Lactobacillus plantarum* LB7c (DSM 17853) and *Lactobacillus plantarum* LB3e (DSM 17852).

A food product containing such viable thermostable *Lactobacillus* strains promoting immunotolerance in autoimmune diseases such as coeliac disease. The identity and deposit numbers of the strains of the present invention are listed here.

The LB931 has been deposited on Jan. 9, 1998 at DSMZ-Deutsche Sammlung von Mikroorganismen und Zellkulturen, Mascheroder Weg 1b D-38124 Braunschweig. It has been assigned accession number DSM11918.

The LB21 has been deposited on Jun. 11, 1993 at NCIMB Ltd, Ferguson Building, Craibstone Estate, Bucksburn, Aberdeen, AB21 9YA, UK. It has been assigned accession number NCIMB 40564.

The LB3e has been deposited on Jan. 6, 2006 at DSMZ-Deutsche Sammlung von Mikroorganismn und Zellkulturen, Mascheroder Weg 1b D-38124 Braunschweig. It has been assigned accession number DSM 17852.

The LB7c has been deposited on Jan. 6, 2006 at DSMZ-Deutsche Sammlung von Mikroorganismen und Zellkulturen, Mascheroder Weg 1b D-38124 Braunschweig. It has been assigned accession number DSM 17853.

The *Lactobacillus* strains mentioned above could be referred to as LB931 (DSM11918), LB21 (NCIMB 40564), LB3e (DSM 17852) and LB7c (DSM 17853).

Food products according to the present invention may comprise one or more strains selected from the above defined LB strains. Other mixtures or single thermostable LB strains could be used advantageously within the scope of the present invention.

Figure 8:
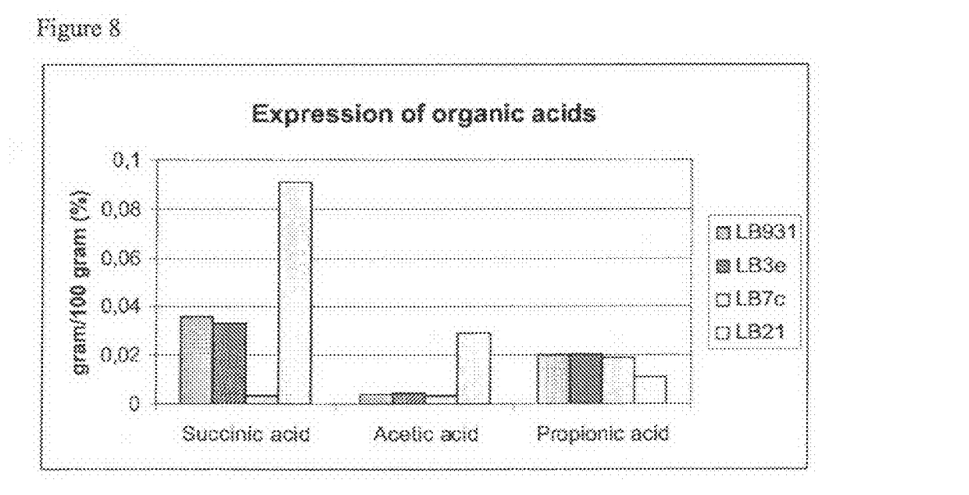
FIG. 8 discloses expression of organic acids in an Auto-Scaled Chromatogram of supernatants of the *Lactobacillus* strains LB931, LB3e, LB7c and LB21 (analysis completed by Steins Laboratorium).
Figure 9:
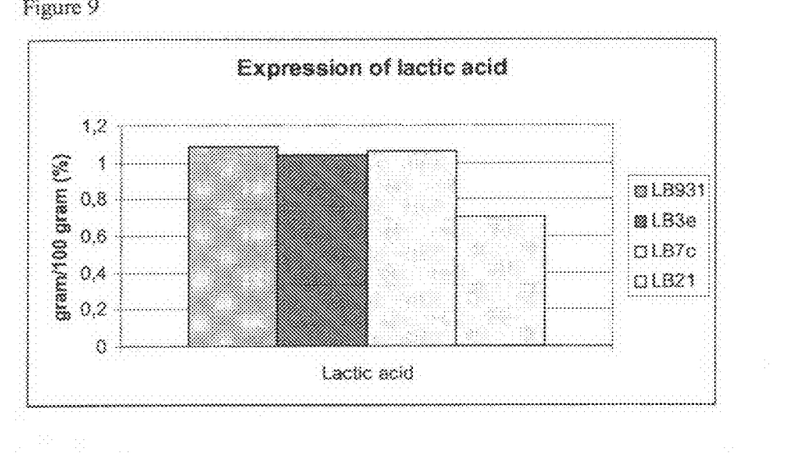
FIG. 9 discloses expression of lactic acids in an Auto-Scaled Chromatogram of supernatants of the *Lactobacillus* strains LB931, LB3e, LB7c and LB21 (analysis completed by Steins Laboratorium).

The above mentioned five four thermostable *Lactobacillus* strains have the ability to survive in a high temperature environment i.e. above +80° C. for more than 25 minutes or alternatively for more than 10 seconds in a microwave radiated environment and still produce substances (which could be soluble, such as lactic acid, succinic acid, acetic acid, and propionic acid) that inhibit the growth of pathogenic microorganisms, such as enterobacteria, group B streptococci, staphylococci and yeast FIG. 8 discloses expression of organic acids and FIG. 9 discloses expression of lactic acids in an Auto-Scaled Chromatogram of supernatants of the *Lactobacillus* strains LB931, LB3e, LB7c and LB21.

These strains are endurable and readily survive long periods of storage in room temperature. Accordingly products containing LB931, LB21, LB3e and LB7c have a long shelf life. The strains can easily be included in different food products.

The ability of the *Lactobacillus* to survive in different applications was determined, see Example 2. No major reduction of the CFU/g was detected in the wholemeal gruel powder preparation with freeze-dried LB931 and LB21 that were stored in +37° for 31 days.

The ability for *Lactobacillus* to survive in snack bars when they are put on oat grains was determined, see Example 3. It is possible to put *Lactobacillus* strains on grains and they will survive for 8 months in room temperature and more than 8 months in +4° C.

Both LB931 and LB21 have the ability to survive in snack bars for 25 days. The snack bars containing LB931 had 7.6× 10⁶ CFU/ml at day 46.

Thus, the thermostable LB strains can endure storage for a long period of time, and it is possible to induce the strain in different kinds of preparations. It could be used in bake-off products.

Figure 1:
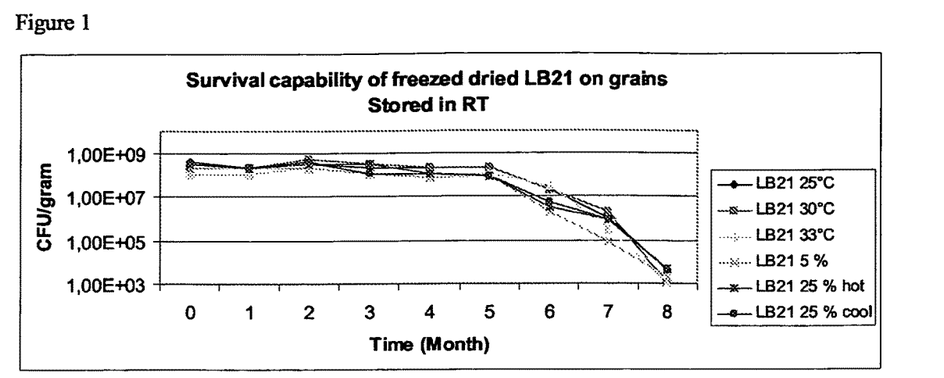
FIG. 1 discloses the survival capability of freeze dried LB21 on grains stored in room temperature.
Figure 2:
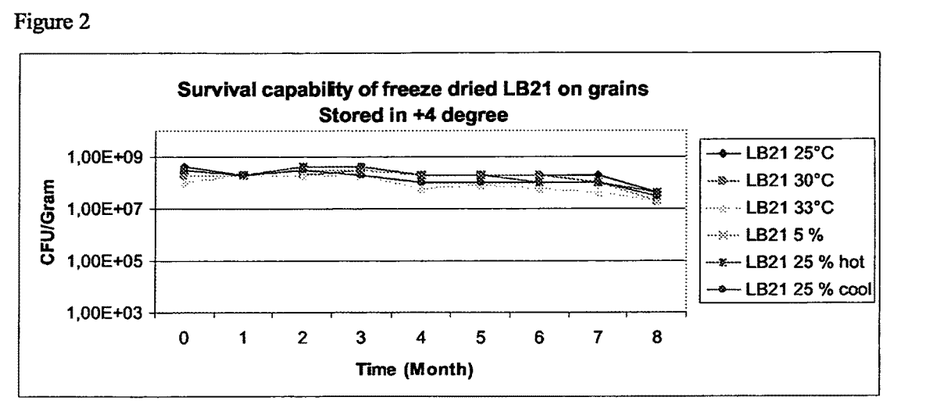
FIG. 2 discloses the survival capability of freeze dried LB21 on grains stored in +4° C.
Figure 3:
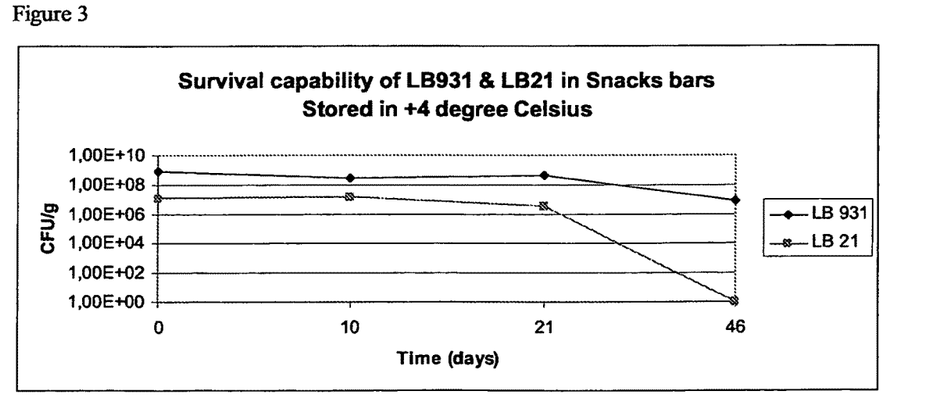
FIG. 3 discloses the survival capability of freeze dried LB931 and LB21 in snack bars stored in +4° C.
Figure 4:
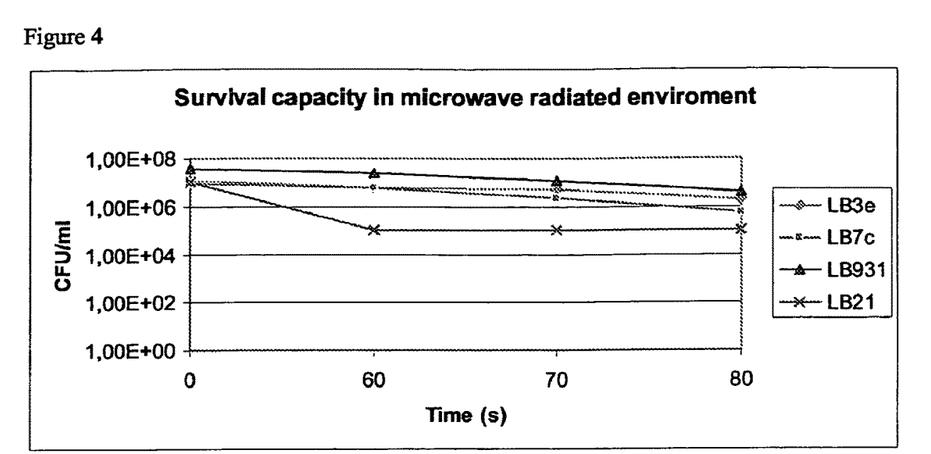
FIG. 4 discloses the survival capability of LB931 and LB21 in microwave radiated environment.

The survival capacity in a microwave radiated environment was also evaluated, see Example 4. Milk cereal drinks were prepared together with the *Lactobacillus* strains at a start concentration of 10⁷ CFU/ml. LB931 showed a higher CFU/ml than LB21 until 80 seconds. The CFU/ml of LB21 remained unchanged from 30 seconds to 90 seconds. The *Lactobacillus* has the ability to survive in cereal products in microwave radiated environment. The results are presented in FIG. 4.

The killing of the four different strains of lactic acid bacteria with UV-light were investigated and an interference test was used to test the four lactic acid strains for their ability to inhibit growth of pathogens and thus also their capacity to function as probiotics, the results are shown in Example 5.

Figure 5:
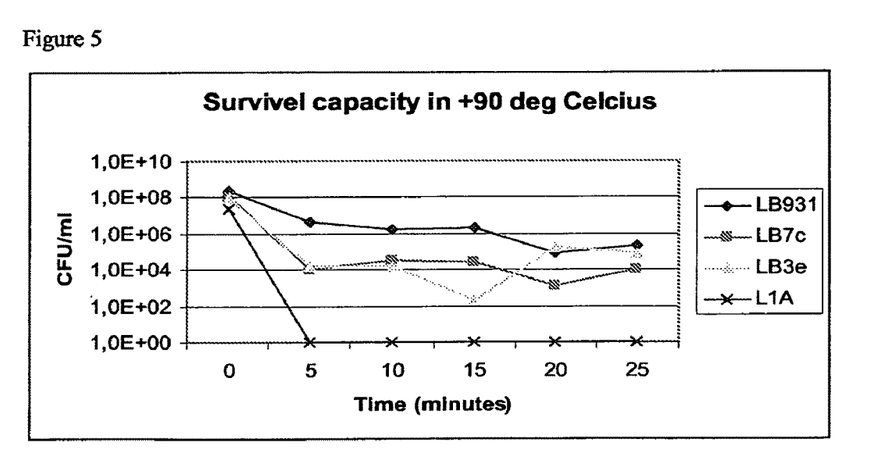
FIG. 5 discloses the survival capability of LB931, LB7c, LB3e and L1A in +80° C.
Figure 6:
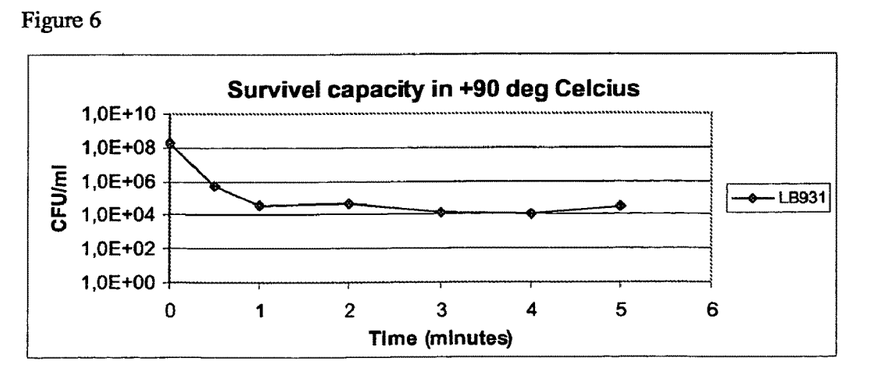
FIG. 6 discloses the survival capability of LB931 in +90° C.
Figure 7:
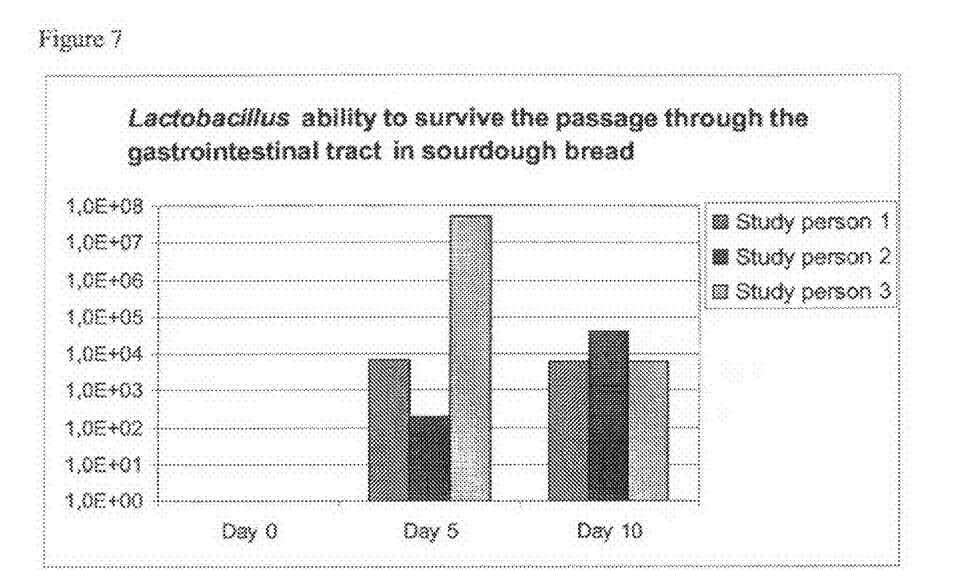
FIG. 7 discloses the *Lactobacillus* ability to survive the passage through the gastrointestinal tract in sourdough bread.

The high temperature resistance of the *Lactobacillus* strains have been investigated, see Example 6. LB931, LB3e and LB7c have the ability to survive in +80° C. for more than 25 minutes and LB931 survives for more than 5 minutes in +90° C. The control strain, L1A, do not even survive for 5 minutes in +80° C. The results are presented in FIGS. 5 and 6.

The growth capacities of the *Lactobacillus* in sourdough starters have been investigated, see Example 7. Two different types of flours, wheat and rye, were used to determine the best environment for the *Lactobacillus*. The type of flour did not affect the outcome of the experiment. The starters increased one log and ended on the same CFU/g independent of the type of flours. As a control, the *Lactococcus* Lactis L1A was used. The L1A did not grow in the starter. The CFU/g had decreased from day 0 to day 3.

In Example 8 the survival of the *Lactobacillus* in bread is shown. The temperatures in different breads were established, see table 13. The survival of the bacteria in the bread was determined at different times, see tables 14-16. *Lactobacillus* Lactis L1A was used as control. All the *Lactobacillus* strains that were tested survived in all the different temperatures and times. The control, L1A, did not survive. There was no visual growth of the bacteria from day 0.

Depending on the food product and the purpose it is desirable that it comprises the viable *Lactobacillus* strain in a sufficient amount that is preferably as high as possible, to provide the desired effects. The experimental results show that amounts above 1.0×10¹⁰ CFU/g can be achieved. In a food product the viable *Lactobacillus* strain should be present in an amount above 1.0×10³ CFU/g, preferably above 1.0× 10⁴ CFU/g and most preferably above 1.0×10⁵ CFU/g, living bacteria per gram of the food product.

An example is a slice of bread that weighs at least 15 gram wherein the viable *Lactobacillus* strain is present in an amount above 1.0×10³ CFU/g, preferably above 1.0×10⁴ CFU/g and most preferably above 1.0×10⁵ CFU/g, living bacteria per gram of a slice of bread.

For example, a viable *Lactobacillus* strain wherein the start concentration is about 1×10⁶ has a CFU above 1×10³ after being exposed to temperatures from +80° C. for more than 25 minutes or alternatively for more than 10 s in a microwave radiated environment.

The capability of *Lactobacillus* to promoting immunotolerance in autoimmune diseases such as coeliac disease has been investigated in in vivo studies. The *Lactobacillus* strains are able to reduce the inflammatory lesion in the upper intestinal mucosa and reduce the levels of antibodies associated with autoimmune diseases. Example 9a, 9b and 9c also indicate that the *Lactobacillus* have the capability to influence the immune system in a positive way. The children that were given the *Lactobacillus* did not experience any symptoms related to the coeliac disease. All the children that were given placebo became ill after 1-3.5 months of challenge with gluten. The biopsy showed normal tissue in the group given *Lactobacillus* and the tissue showed indication of inflammation in the group given placebo. Products according to the invention may comprise one or more strains selected from the above defined group. Other mixtures or single LB strains could advantageously be used within the scope of the present invention.

The present invention will now be described in reference to the following examples, which should not be regarded as limiting for the scope of the invention.

EXAMPLES

Example 1

Isolation and Identification of the *Lactobacillus* Strains

LB931 was isolated from a healthy woman. The strain was classified as *Lactobacillus plantarum* according to the test kit API 50 CH (API systems, BioMerieux, FR), and was denominated LB931. The strain was further typed by DNA-analysis with SDS-page at BCCM/LMG (Belgium) to be *Lactobacillus plantarum-pentosus-plantarum*.

LB21 was isolated from a healthy baby. The strain was classified as *Lactobacillus rhamnosus* according to the test kit API 50 (API systems, BioMerieux, FR), and was denominated LB21. The strain was further typed by DNA-analysis with SDS-page at NCIMB (UK) to be *Lactobacillus rhamnosus*.

LB3e was isolated from human. The strain was classified as *Lactobacillus plantarum* according the kit API 50 (API systems, BioMerieux, FR), and was denominated LB3e. The strain was further typed by 16S rDNA gene sequence at DSMZ (Germany) to be *Lactobacillus plantarum*.

LB7c was isolated from human. The strain was classified as *Lactobacillus plantarum* according the kit API 50 (API systems, BioMerieux, FR), and was denominated LB7c. The strain was further typed by 16S rDNA gene sequence at DSMZ (Germany) to be *Lactobacillus plantarum*.

Example 2

The Survival Capabilities of *Lactobacillus* in Different Preparations a) Skim milk preparations of LB931 were freeze-dried according to standard methods. To determine the durability of the preparations the obtained powder was stored in wholemeal gruel powder at +37° C. for 31 days to symbolise storage in room temperature for 6 month. The number of bacteria was determined after 31 days and the results are disclosed in table 1 below.

TABLE 1

| Days | No. of bacteria CFU/g |
|---|---|
| Day 0 | $7.0 \times 10^{11}$ |
| Day 31 | $1.0 \times 10^{11}$ | b) LB931 dissolved in a suspension of equal parts skim milk and 0.9% NaCl. The dissolved bacteria were then incubated at different temperatures. The amount of bacteria was continuously monitored by cell counting. The results are disclosed in table 2 below.

TABLE 2

| | No. of bacteria CFU/ml | | | |
|---|---|---|---|---|
| Temperature, ° C. | Day 0 | Day 2 | Day 5 | Day 32 |
| 4 | $7.8 \times 10^{10}$ | | | $2.2 \times 10^{10}$ |
| 20 | $1.8 \times 10^{10}$ | | $2.2 \times 10^{10}$ | |
| 27 | $1.8 \times 10^{10}$ | $1.2 \times 10^{10}$ | $3.3 \times 10^{9}$ | |

The results show that LB931 is stable in a mixture of skim milk and NaCl for a period of one month at +4° C.

c) A skim milk preparation of LB931 was freeze-dried according to standard methods. The obtained powder was stored in Petri dishes at room temperature and at +6° C. The number of bacteria was determined after 7 days and 25 days, respectively. The results are disclosed in table 3 below.

TABLE 3

| | No. of bacteria CFU/g | | |
|---|---|---|---|
| Temperature ° C. | Day 0 | Day 7 | Day 25 |
| 6 | $4.2 \times 10^{8}$ | $2.2 \times 10^{8}$ | $1.2 \times 10^{8}$ |
| 22 | $4.2 \times 10^{8}$ | $1.9 \times 10^{8}$ | $1.4 \times 10^{8}$ |

The number of bacteria in the freeze-dried powder was also monitored every fourth week up to 68 weeks. After one year, at +6° C., more than $10^{5}$ CFU/g LB931 could be found.

d) A skim milk preparation of LB21 was freeze-dried according to standard methods. The obtained powder was stored in a glass bottle at +4° C. The number of bacteria was determined after 0, 10, 40 and 365 days, respectively. The results are disclosed in table 4 below.

TABLE 4

| | Day 0 | Day 10 | Day 40 | Day 365 |
|---|---|---|---|---|
| LB21 | $2.3 \times 10^{10}$ | $2.3 \times 10^{10}$ | $1.0 \times 10^{10}$ | $1.2 \times 10^{10}$ |

Example 3

The Survival Capabilities of *Lactobacillus* in Different Oats Products a) A freeze-dried preparation of LB21 was put on rolled oats. Six different methods were used to put the bacteria on the grains. The freeze-dried LB21 were mixed with maltodextrin/glucose so they would stick to the grains. The bacteria were put on the grains at different temperatures and were also dried in different temperature to find the best method. The results are shown in Table 5.

TABLE 5

|  | Preparation temperature | | Dry |
| --- | --- | --- | --- |
|  | Air | Oil | Air |
| LB21 25° C. | +25° C. | — | +30° C. |
| LB21 30° C. | +30° C. | — | +38° C. |
| LB21 33° C. | +33° C. | — | +38° C. |
| LB21 5% | +29° C. | +38° C. | +38° C. |
| LB21 25% hot | +28° C. | +38° C. | +38° C. |
| LB21 25% cool | +28° C. | +27° C. | +25° C. |

The grains with bacteria were stored in both +25° C. and in +4° C. for 244 days. The Survival capability was determined once a month. The results are disclosed in tables 6-7 below.

TABLE 6

Stored in +25° C.

No. of bacteria CFU/g

| Time (days) | LB21 25° C. | LB21 30° C. | LB21 33° C. | LB21 5% | LB21 25% hot | LB21 25% cool |
| --- | --- | --- | --- | --- | --- | --- |
| 6 | $4 \times 10^8$ | $2 \times 10^8$ | $1 \times 10^8$ | $2 \times 10^8$ | $3 \times 10^8$ | $3 \times 10^8$ |
| 31 | $2 \times 10^8$ | $2 \times 10^8$ | $1 \times 10^8$ | $2 \times 10^8$ | $2 \times 10^8$ | $2 \times 10^8$ |
| 59 | $3 \times 10^8$ | $5 \times 10^8$ | $2 \times 10^8$ | $2 \times 10^8$ | $3 \times 10^8$ | $4 \times 10^8$ |
| 90 | $2 \times 10^8$ | $3 \times 10^8$ | $1 \times 10^8$ | $1 \times 10^8$ | $3 \times 10^8$ | $1 \times 10^8$ |
| 122 | $2 \times 10^8$ | $2 \times 10^8$ | $7 \times 10^7$ | $7 \times 10^7$ | $1 \times 10^8$ | $1 \times 10^8$ |
| 144 | $2 \times 10^8$ | $2 \times 10^8$ | $1 \times 10^8$ | $8 \times 10^7$ | $8 \times 10^7$ | $8 \times 10^7$ |
| 180 | $2 \times 10^7$ | $2 \times 10^7$ | $3 \times 10^7$ | $2 \times 10^6$ | $3 \times 10^6$ | $5 \times 10^6$ |
| 219 | $1 \times 10^6$ | $2 \times 10^6$ | $3 \times 10^5$ | $8 \times 10^4$ | $9 \times 10^5$ | $9 \times 10^5$ |
| 244 | $4 \times 10^3$ | $1 \times 10^3$ | $1 \times 10^3$ | $2 \times 10^3$ | $5 \times 10^3$ | $6 \times 10^3$ |

TABLE 7

Stored in +4° C.

No. of bacteria CFU/g

| Time (days) | LB21 25° C. | LB21 30° C. | LB21 33° C. | LB21 5% | LB21 25% hot | LB21 25% cool |
| --- | --- | --- | --- | --- | --- | --- |
| 6 | $4 \times 10^8$ | $2 \times 10^8$ | $1 \times 10^8$ | $2 \times 10^8$ | $3 \times 10^8$ | $3 \times 10^8$ |
| 31 | $2 \times 10^8$ | $2 \times 10^8$ | $2 \times 10^8$ | $2 \times 10^8$ | $2 \times 10^8$ | $2 \times 10^8$ |
| 59 | $4 \times 10^8$ | $2 \times 10^8$ | $2 \times 10^8$ | $3 \times 10^8$ | $4 \times 10^8$ | $3 \times 10^8$ |
| 90 | $4 \times 10^8$ | $2 \times 10^8$ | $2 \times 10^8$ | $3 \times 10^8$ | $4 \times 10^8$ | $2 \times 10^8$ |
| 122 | $2 \times 10^8$ | $2 \times 10^8$ | $6 \times 10^7$ | $2 \times 10^8$ | $2 \times 10^8$ | $1 \times 10^8$ |
| 144 | $2 \times 10^8$ | $2 \times 10^8$ | $8 \times 10^7$ | $2 \times 10^8$ | $2 \times 10^8$ | $1 \times 10^8$ |
| 180 | $2 \times 10^8$ | $2 \times 10^8$ | $6 \times 10^7$ | $1 \times 10^8$ | $1 \times 10^8$ | $1 \times 10^8$ |
| 219 | $2 \times 10^8$ | $1 \times 10^8$ | $4 \times 10^7$ | $1 \times 10^8$ | $1 \times 10^8$ | $1 \times 10^8$ |
| 244 | $4 \times 10^8$ | $2 \times 10^8$ | $2 \times 10^7$ | $2 \times 10^8$ | $4 \times 10^8$ | $3 \times 10^7$ | b) Snack bars were made with LB931 and LB21. Each bar weighed 25 g before they were split in 4 pieces. Each piece was put in a sterile bag in +4° C. The number of bacteria was determined after 0, 10, 21 and 46 days. The results are disclosed in table 8 below.

TABLE 8

No. of bacteria CFU/g

| Time (days) | LB931 | LB21 |
| --- | --- | --- |
| 0 | $8 \times 10^8$ | $1.2 \times 10^7$ |
| 10 | $2.7 \times 10^8$ | $1.3 \times 10^7$ |
| 21 | $3.8 \times 10^8$ | $3.0 \times 10^5$ |
| 46 | $7.6 \times 10^6$ | 0 |

Thermostable LB strains can survive in high temperature in different cereal preparations.

Example 4

The Survival Capabilities of *Lactobacillus* in Microwave Radiated Environment

A freeze-dried preparation of LB931 was included in the conventional milk cereal drink powder and in porridge oats. The milk cereal drink and the porridge oats were prepared according to the instruction on the package resulting in a volume of about 200 ml. A microwave oven (850 W) with the internal measurement 30×29×20 cm was used as the source of heat. Thus, the internal volume of the microwave oven was approximately 17 $dm^3$. The number of bacteria was determined after 30 seconds, 60 seconds, 70 seconds, 80 seconds and 90 seconds, respectively. The temperature of the milk cereal drink after 90 seconds in the microwave oven was about +60° C. The procedure was repeated with overnight culture of LB21. The thermostable LB strains are able to survive in microwave radiated environment. The results are disclosed in table 9 below.

TABLE 9

No. of bacteria CFU/ml

| Time (s) | LB931 | LB21 |
| --- | --- | --- |
| 0 | $3.5 \times 10^7$ | $1.1 \times 10^7$ |
| 30 | $2.2 \times 10^7$ | $2.2 \times 10^5$ |
| 60 | $2.6 \times 10^7$ | $1.0 \times 10^5$ |
| 70 | $1.3 \times 10^7$ | $1.0 \times 10^5$ |
| 80 | $3.9 \times 10^6$ | $1.0 \times 10^5$ |
| 90 | $1.1 \times 10^3$ | $1.0 \times 10^5$ |

Example 5

The killing of the four different strains of lactic acid bacteria with UV-light were investigated. The four different stains of lactic acid bacteria *Lactobacillus plantarum*; LB931 (isolated from urinary tract of human), LB3e (isolated from saliva of child), LB7c (isolated from tooth surface of child) and LB21 (isolated from faeces of newborn children) used in this example were spread on MRS-agar plates and incubated for 20 h at 37° C., 5% $CO_2$. They were then inoculated in 3 ml MRS-broth at 37° C., 5% $CO_2$ over night which generates about $10^9$ CFU/ml. The overnight cultures of the strains were added to a final volume of 1% in MRS broth and were incubated for 20 h at 37° C., 5% $CO_2$ The bacteria were centrifuged (3800 rpm, 20 min, +4° C.) and then washed 2 times in 10 ml 0.9% NaCl. The bacteria were dissolved in 0.9% NaCl. The concentration of the bacteria was determined by colony-forming unit (CFU) counting. The bacteria were irradiated for different times at a distance of 5 cm from a UVC-lamp (Kendro laboratory products, 2×15 W, 254 nm). Lactic acid bacteria LB7c and LB21 were irradiated for 9 h while lactic acid bacteria LB3c and LB931 were irradiated for 10 h. The death of the bacteria was controlled on MRS agar plates, incubated for 48 h at 37° C., 5% $CO_2$.

Agar Overlay-Interference Test

An interference test was used to test the four lactic acid strains (see table 10 for their ability to inhibit growth of pathogens. The four *Lactobacillus* strains in table 10 were inoculated in 3 ml MRS broth and then incubated in 37° C., 5% $CO_2$ for 20 h. 1 ml of the cultures were mixed with 23 ml MRS agar together with 2 ml 7.5M NaAc, the plates were thereafter incubated for 20 h in 37° C., 5% $CO_2$. Nine different interference test strains (ITS) (NUS, Umeå, Sweden), isolated from people with urinary infections, were inoculated in M17 broth and incubated in 37° C. over night. A second agar layer of 25 ml M17 with 750 µl 6.5M $KH_2PO_4$ was found over the first one. The test strains, in stationary phase, were replicated with help of a Steers steel pin (Steers et al., 1959) on the M17 agar surface and also on a control plate and then incubated in 37° C., 5% $CO_2$ over night.

Inhibition of Pathogens by Lactic Acid Bacteria

An interference test was done to test the four lactic acid bacteria strains for their ability to inhibit pathogens and thus also their capacity to function as probiotics. The result from this test is shown in table 10. LB931 totally inhibited all 8 pathogens tested. LB3, LB7 and LB21 showed total inhibition of all pathogens except for *Candida albicans*, which were partly inhibited. *Lactobacillus acidophilus* was used as control.

TABLE 10

Inhibition of pathogens by lactic acid bacteria

| Strain tested | LB931 | LB3e | LB7c | LB21 | L. acidophilus 2060V |
|---|---|---|---|---|---|
| Candida albicans | − | − | − | − | + |
| Klebsiella species | − | ± | ± | ± | + |
| Staphylococcus aureus | − | − | − | − | + |
| Coagulase-negative staphylococcus | − | − | − | − | ? |
| Enterococcus faecalis | − | − | − | − | + |
| Enterobacteriaceae species | − | − | − | − | ? |
| Proteus mirabilis | − | − | − | − | ? |
| Escherichia coli | − | − | − | − | + |

+, no inhibition; ±, partly inhibition; −, total inhibition; ?, not done

Example 6

The Survival Capabilities of *Lactobacillus* in Different Temperatures a) Different suspensions of *Lactobacillus* were made of freeze-dried LB931 in NaCl 0.9% and overnight culture of LB931, LB7c, LB3e and L1A. The suspensions were at $10^9$-$10^{11}$ CFU/ml. 5 ml of NaCl 0.9% was heated up to +80° C. in a water bath. As soon as the NaCl was +80° C. 100 µl of bacteria suspension was added. The number of bacteria was determined after 5 minutes, 10 minutes, 15 minutes, 20 minutes and 25 minutes, respectively. The results are disclosed in table 11 below (NVG=no visible growth).

TABLE 11

| | No. of bacteria CFU/ml | | | |
|---|---|---|---|---|
| Time (min) | LB931 | LB7c | LB3e | L1A |
| 0 | $2.30 \times 10^8$ | $1.1 \times 10^8$ | $9.7 \times 10^7$ | $2.5 \times 10^7$ |
| 5 | $4.33 \times 10^6$ | $1.0 \times 10^4$ | $1.4 \times 10^4$ | NVG |
| 10 | $1.77 \times 10^6$ | $3.3 \times 10^4$ | $1.4 \times 10^4$ | NVG |
| 15 | $2.00 \times 10^6$ | $2.5 \times 10^4$ | $1.8 \times 10^2$ | NVG |
| 20 | $8.20 \times 10^4$ | $1.2 \times 10^3$ | $1.9 \times 10^5$ | NVG |
| 25 | $2.24 \times 10^5$ | $1.0 \times 10^4$ | $7.8 \times 10^4$ | NVG | b) +80° C. in more than 20, 30, 40, 50, 60 minutes 5 ml of MRS were heated to +85° C. in a water bath. 500 µl of a overnight culture was added to the suspension. The ability to survive was determined after 20, 30, 40, 50 and 60 minutes respectively. The results are shown in table 12 below.

TABLE 12

| | No. of bacteria CFU/ml | | | |
|---|---|---|---|---|
| Time (min) | LB3e | LB7c | LB931 | LB21 |
| 20 | VG | VG | VG | VG |
| 30 | VG | VG | VG | VG |
| 40 | VG | VG | VG | VG |
| 50 | VG | VG | VG | VG |
| 60 | VG | VG | VG | VG |

VG = visible growth c) A suspension of LB931 was prepared by suspending freeze-dried LB931 in NaCl 0.9% and also an overnight culture of LB931. The NaCl was heated up to +90° C. in a water bath. As soon as the NaCl was +80° C. 100 µl of bacteria suspension was added. The number of bacteria was determined after 0.5 minutes, 1 minutes, 2 minutes, 3 minutes, 4 minutes and 5 minutes, respectively. The results are disclosed in table 13 below.

TABLE 13

| Time (min) | No. of bacteria CFU/ml LB931 |
|---|---|
| 0 | $1.76 \times 10^8$ |
| 0.5 | $5.00 \times 10^5$ |
| 1 | $3.54 \times 10^4$ |
| 2 | $4.43 \times 10^4$ |
| 3 | $1.25 \times 10^4$ |
| 4 | $1.14 \times 10^4$ |
| 5 | $3.00 \times 10^4$ | d) A freeze-dried preparation of LB931 and LB21 was included in the conventional milk cereal drink powder and in porridge oats. The milk cereal drink was prepared according to the instruction on the package. The stove was used as the source of heat The number of bacteria was determined after the milk cereal drink was warmed up to +37° C. The results are disclosed in table 14 below.

TABLE 14

| | No. of bacteria CFU/ml | |
|---|---|---|
| Temperature (° C.) | LB931 | LB21 |
| 10 | $2.9 \times 10^7$ | $3.0 \times 10^7$ |
| 37 | $2.4 \times 10^7$ | $2.8 \times 10^7$ |

Example 7

The Survival Capabilities of *Lactobacillus* in Sourdough Starter a) Different sourdough starters were made of wheat flour containing different strains of *Lactobacillus* and *Lactococcus*. Flour and water was mixed to a volume of 3 dl. 10 ml of thawed bacteria suspension was included in the starters. The sourdough starters were kept in room temperature for 3 days. Everyday the sour-dough starters were given more honey, flour and water. The number of bacteria was determined after 3 days. After the 3 days in room temperature the starters were put in +4° C. for 6 days. The number of bacteria was determined after 3 days, and 6 days, respectively. The results are disclosed in tables 15-16 below.

TABLE 15

| | No. of bacteria CFU/g | | |
|---|---|---|---|
| Time (days) | LB931 +25° C. | LB7c +25° C. | LB3e +25° C. |
| 0 | $5 \times 10^8$ | $2 \times 10^7$ | $6 \times 10^7$ |
| 3 | $3 \times 10^9$ | $9 \times 10^8$ | $2 \times 10^9$ |

TABLE 16

| | No. of bacteria CFU/g | | |
|---|---|---|---|
| Time (days) | LB931 + 4° C. | LB7c + 4° C. | LB3e + 4° C. |
| 0 | $3 \times 10^9$ | $6 \times 10^8$ | $3 \times 10^9$ |
| 3 | $2 \times 10^9$ | $3 \times 10^8$ | $9 \times 10^8$ |
| 6 | $2 \times 10^9$ | $2 \times 10^7$ | $8 \times 10^8$ | b) Different sourdough starters were made of rye flour containing different strains of *lactobacillus*. Flour and water was mixed to a volume of 3 dl. 10 ml of thawed bacteria suspension was included in the starters. The sourdough starters were kept in room temperature for 3 days. The sourdough starters were everyday given more honey, flour and water. The number of bacteria was determined after 3 days. Then the starters were kept in +4° C. for 6 days. The number of bacteria was determined after 3 days and 6 days, respectively. The results are disclosed in table 17-18 below.

TABLE 17

| | No. of bacteria CFU/g stored in +25° C. | | | |
|---|---|---|---|---|
| Time (days) | LB931 | LB7c | LB3e | L1A |
| 0 | $2 \times 10^8$ | $2 \times 10^7$ | $6 \times 10^7$ | $1 \times 10^7$ |
| 3 | $7 \times 10^9$ | $9 \times 10^8$ | $2 \times 10^9$ | $8 \times 10^5$ |

TABLE 18

| | No. of bacteria CFU/g stored in +4° C | | |
|---|---|---|---|
| Time (days) | LB931 | LB7c | LB3e |
| 0 | $3 \times 10^9$ | $6 \times 10^8$ | $3 \times 10^9$ |
| 3 | $2 \times 10^9$ | $3 \times 10^8$ | $9 \times 10^8$ |
| 6 | $2 \times 10^9$ | $2 \times 10^7$ | $8 \times 10^8$ |

Example 8

The Survival Capabilities of *Lactobacillus* in Bread, Visual Detection of Mould in the Bread and Isolation of *Lactobacillus* in Stool Samples a) A sourdough was prepared with 1 dl wheat sourdough starter containing LB931, water, flour of wheat and rye to a total volume of 6 dl. The dough was rising 2×45 minutes and baked at the temperature between 230-240° C. for 25-30 minutes. The temperature in the bread was measured after the bread was taken out of the oven, 5 minutes, 10 minutes, 15 minutes and 20 minutes, respectively. The results are disclosed in table 19 below.

TABLE 19

| Time (minutes) | Baked in 230° C. for 25 minutes | Baked in 230° C. for 35 minutes | Baked in 240° C. for 30 minutes |
|---|---|---|---|
| 0 | 97.6° C. | 99.4° C. | 97.6° C. |
| 5 | Not done | Not done | 86.3° C. |
| 10 | Not done | Not done | 78.0° C. |
| 15 | Not done | Not done | 68.1° C. |
| 20 | Not done | Not done | 62.7° C. | b) Sourdough bread was baked with thermostable *Lactobacillus*. The survival of the bacteria in the bread was determined after 2 days, 3 days, 4 days, 6 days and 7 days, respectively. The results are disclosed in tables 20-25 below.

TABLE 20

| Baked in +230° C. for 20 minutes (Sourdough starter) | | |
|---|---|---|
| | No. of bacteria CFU/g | |
| Time (days) | LB3e (rye) | LB7c (wheat) |
| 0 | $1.1 \times 10^5$ | $1.2 \times 10^4$ |
| 5 | $1.1 \times 10^4$ | $2.1 \times 10^5$ |

TABLE 21

| Baked in +230° C. for 25 minutes (Rye Sourdough starter) | | | | |
|---|---|---|---|---|
| | No. of bacteria CFU/g | | | |
| Time (days) | LB931 | LB3e | LB7c | LB21 |
| 0 | $9 \times 10^3$ | $3 \times 10^3$ | $7 \times 10^2$ | $7 \times 10^3$ |
| 3 | $1 \times 10^5$ | $5 \times 10^4$ | $1 \times 10^4$ | $3 \times 10^4$ |
| 7 | $9 \times 10^4$ | $6 \times 10^4$ | $9 \times 10^4$ | Not done |

TABLE 22

| Baked in +230° C. for 35 minutes (Rye Sourdough starter) | | | |
|---|---|---|---|
| | No. of bacteria CFU/g | | |
| Time (days) | LB931 | LB3e | LB7c |
| 0 | $9 \times 10^2$ | $2 \times 10^2$ | $1 \times 10^2$ |
| 3 | $8 \times 10^3$ | $3 \times 10^3$ | $7 \times 10^3$ |
| 7 | $9 \times 10^3$ | $7 \times 10^3$ | $6 \times 10^3$ |

TABLE 23

| Baked in +240° C. for 30 minutes growth | | |
|---|---|---|
| | No. of bacteria CFU/g | |
| | Wheat Sourdough starter | Rye Sourdough starter |
| Time (days) | LB931 | L1A | LB931 |
| 0 | $4 \times 10^3$ | No Visible Growth (NVG) | $3 \times 10^4$ |
| 2 | $6 \times 10^4$ | NVG | $7 \times 10^4$ |
| 4 | $2 \times 10^5$ | NVG | $9 \times 10^5$ |
| 6 | $1 \times 10^5$ | NVG | $6 \times 10^5$ |
| 8 | $7 \times 10^4$ | NVG | $8 \times 10^4$ | c) Bread was made of wheat flour containing the strain LB21. Warm water, honey, yeast, salt, wheat and 5 ml LB21 at CFU $1 \times 10^9$ were combined in a large mixer bowl to a total volume of 1 litre. The CFU/ml of the dough was 1×10$^6$. The dough was kneaded for 10 minutes until it pulled away from the sides of the bowl and felt soft, pliable and smooth. The dough was covered and left to rise for 1 hour. The large batch was divided into smaller parts. The dough was covered again and was left for 45 minutes to rise. The bread was baked in 220° C. for 20 minutes and cooled on a rack. The survival of the bacteria in the bread was determined after 0 days and 3 days respectively. The results are disclosed in table 24 below.

TABLE 24

| Time (days) | No. of bacteria CFU/g LB21 |
|---|---|
| 0 | $2 \times 10^3$ |
| 3 | $6 \times 10^3$ |

Possible the CFU/g could be higher if the bread can be cooled faster after baking.

d) Visual detection of mould in the bread, no visual growth (NVG).

Slices of bread containing *Lactobacillus* were kept in air tight plastic bags. The bags were check each day and the growths of mould were determined. The results are disclosed in table 25 below.

TABLE 25

| | Bread | No. of bacteria CFU/g day 15 | Detection of mould |
|---|---|---|---|
| LB931 | Sourdough bread | $5 \times 10^4$ | NVG Day 15 |
| | Sourdough bread | $5 \times 10^4$ | NVG Day 15 |
| LB21 | Sourdough bread | $7.6 \times 10^4$ | NVG Day 15 |
| | Bread with 5 ml bacterial solution | $1.2 \times 10^3$ | NVG Day 15 |
| LB3e | Sourdough bread | $4 \times 10^4$ | NVG Day 15 |
| LB7c | Sourdough bread | $6 \times 10^4$ | NVG Day 15 | e) 3 healthy individuals consumed bread containing LB931, LB21, LB3e and LB7c for ten consecutive days, the strains could be recovered from stool samples in all 3 of the tested volunteers. The results are disclosed in table 26 below.

TABLE 26

| | Day 0 | Day 5 | Day 10 |
|---|---|---|---|
| Study person 1 | 0 | $7 \times 10^3$ | $6 \times 10^3$ |
| Study person 2 | 0 | $2 \times 10^2$ | $4 \times 10^3$ |
| Study person 3 | 0 | $5 \times 10^7$ | $6 \times 10^3$ |

Example 9 a) A case study was made of a nine year old girl who was diagnosed with coeliac disease (CD). She was given *Lactobacillus* (LB21) daily in a high concentration (10$^{10}$ CFU/day) for 3 months before being challenged with gluten. Her antibody levels of endomysium, transglutaminas and total IgA were measured before and each month for the first year and once a year for 6 years. Since she had been on a restricted diet for many years before the study no antibodies were detected before the study started. In the beginning she was given a low concentration of gluten (0.1 g gluten/day/kg bodyweight) but after 4 months she was eating a normal diet. The levels of endomysium and transglutaminas were normal during this time and she did not experience any celiac symptoms. A biopsy of the small intestine was performed when the girl was 13 years old. The results showed no inflamed mucosa tissue and her antibody levels were normal.

b) A pilot study with 4 children suffering from CD was performed. The children were divided into two groups. Group 1 was given *Lactobacillus* (LB21) with 10$^{10}$ CFU/day and group 2 was given placebo. Both groups were challenged with gluten following a standardized scale. The children were given 0.1 g gluten/day/kg bodyweight for 4 weeks and 0.2 g gluten/day/kg bodyweight thereafter. The antibody levels of endomysium, transglutaminas and total IgA were measured during the study. If the antibody levels of the children increased or if the CD symptoms enhanced, a biopsy of the small intestine was performed. The two children in the placebo group became ill after 1-3.5 months of challenged gluten diet. The biopsy showed damage to the mucous membrane of the small intestine. The children also had increased levels of endomysium, transglutaminas and total IgA. The two children in the active group did not experience any symptoms and the levels of endomysium, transglutaminas and total IgA were normal. After 7 months of active treatment a biopsy of the small intestine was performed. The biopsy showed normal intestinal tissue.

c) A study with 10 children suffering from CD was performed. The children were given *Lactobacillus* (LB21) of 10$^{10}$ CFU/day. The children were challenged with gluten following a standardized scale. The children were given 0.025 g gluten/day/kg bodyweight for 2 months and 0.05 g gluten/day/kg bodyweight thereafter. The antibody levels of endomysium, transglutaminas and total IgA were measured during the study. If the CD symptoms enhanced, a biopsy of the small intestine was performed to confirm the typical CD lesions. The children did not experience any symptoms during the study and after 12 months of gluten challenge under intervention of LB21 the children still were healthy and symptom-free, and had normal growth Example 10

Method

An in vitro test was done to evaluate the potential immunomodulatory characteristics of the four different *lactobacillus* strains. Venous blood was collected from healthy women and the peripheral blood mononuclear cells (PBMC) were isolated using Ficoll-Paque gradient. The T cells were polyclonally activated using mAb anti-CD 3 and mAb anti-CD 28. The PBMC and the probiotic bacteria were then mixed in ratio 1:1. Live, dead and isolated supernatants were used to investigate whether it is the bacteria itself or some substances it produces that influences the immune system. The sample set-up was done twice; one set-up was incubated for 6 h and the other set-up was incubated for 18 h. After 6 h incubation, total RNA was isolated and used for the quantification of cytokines at mRNA levels using real-time quantitative reverse transcriptase-polymerase chain reaction. The supernatants from the samples incubated for 18 h were isolated and used for quantification on protein levels with cytometric bead array.

Results

Figure 10:
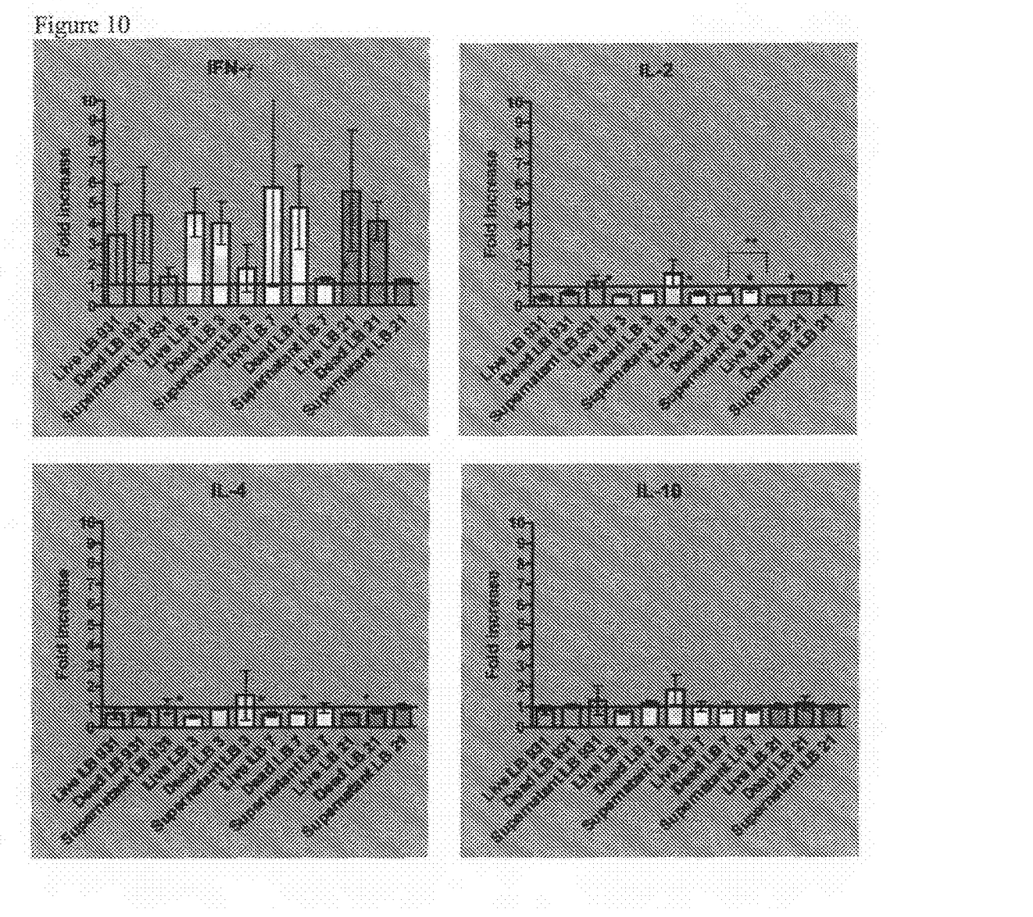
FIG. 10 discloses the production of cytokines by polyclonal activated T cells in the presence of the probiotic bacteria strains LB931, LB3, LB7 and LB21.
Figure 11:
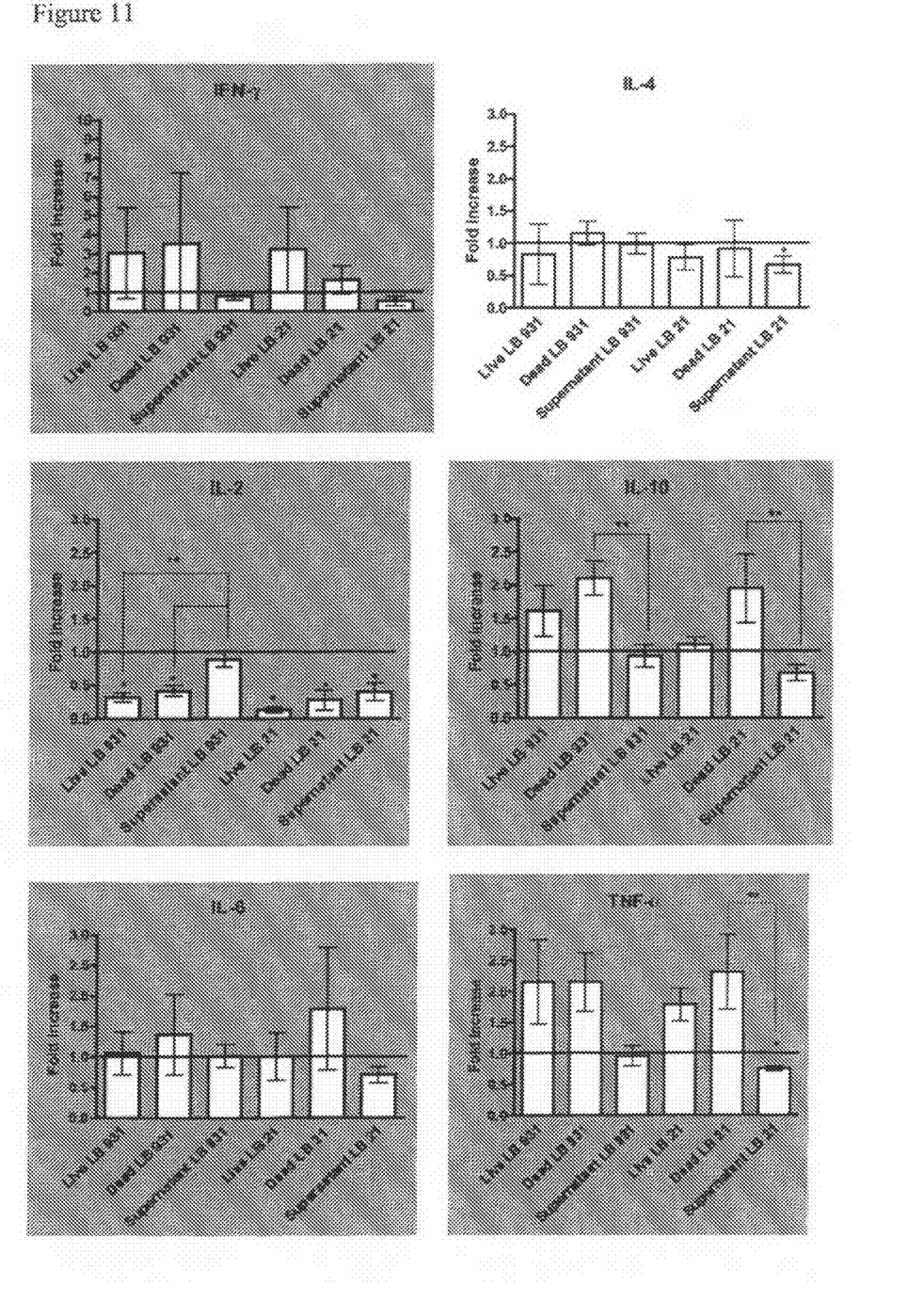
FIG. 11 discloses that both live LB931 and live LB21 gave the same cytokine responses on activated T cells.

FIG. 10 shows the production of cytokines by polyclonal activated T cells in the presence of the probiotic bacteria strains LB931, LB3, LB7 and LB21. Data are from three blood donors and the vertical lines show activated T cells without any stimulation with probiotics and act as a negative control. All four strains show the same responses for the four cytokines measured at mRNA level. The same pattern is also seen at protein levels, where two of the four strains were measured. As seen in FIG. 11 both live LB931 and live LB21 gave the same cytokine responses on activated T cells. Dead LB931 and dead LB21 also follow each other when it comes to increase in cytokine levels. From FIGS. 10 and 3 it can be seen that it is the live *lactobacillus* and dead *lactobacillus* that increase or decrease the cytokine responses of activated T cells. Supernatants isolated from the five different *lactobacillus* strains did not influence the cytokine responses from human T cells at all.

Figure 12:
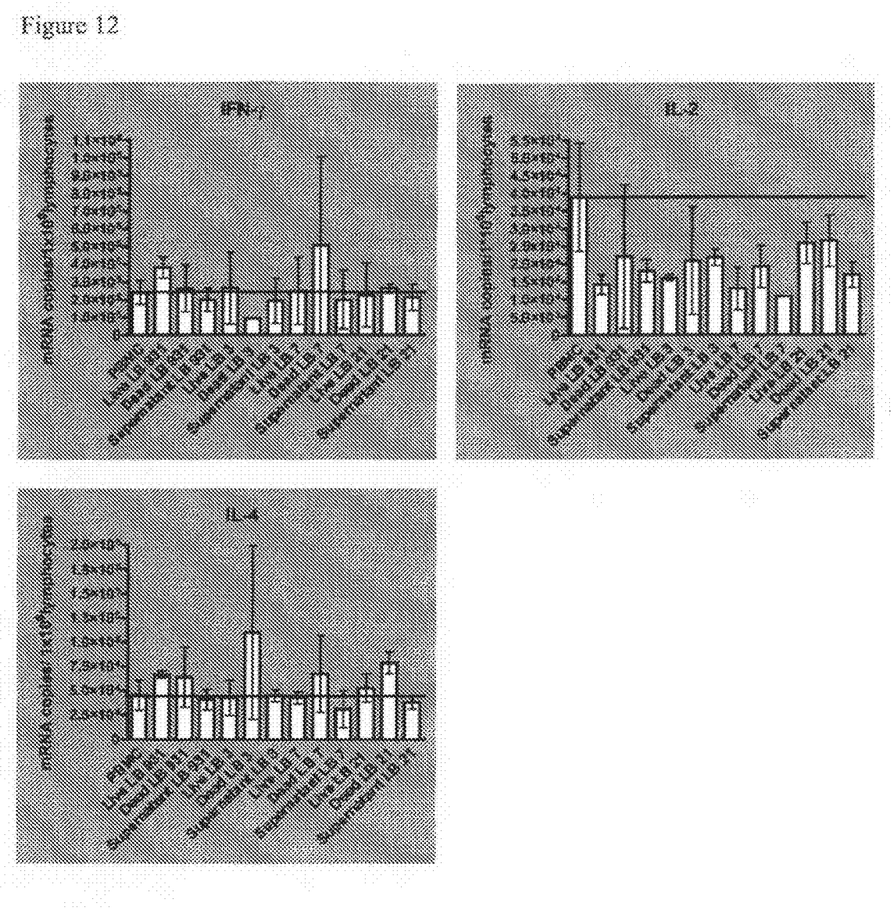
FIG. 12 discloses that the *lactobacillus* did not increase the IFN-γ levels or IL-4 levels of resting T cells.

The *lactobacillus* did not increase the IFN-γ levels or IL-4 levels of resting T cells remarkable as seen in FIG. 12. This shows that none of the four lactic acid bacteria strains have the ability to influence resting T cells.

No statistically significant differences between the four *lactobacillus* strains were found using Tukey's Multiple Comparison Test. This test together with the results from the cytokine responses indicating that LB931, LB3, LB7, LB21 strains are alike.

The invention claimed is:

1. Isolated microorganisms of the *Lactobacillus* strain chosen from the species *Lactobacillus plantarum* LB3e and *Lactobacillus plantarum* LB7c which have been deposited at Deutsche Sammlung von Mikroorganismen and Zeelkulturen, and have been assigned accession number 17852 and 17853 respectively that are able to survive temperatures from +80° C. for more than 25 minutes.

2. A food product selected from the group consisting of bread, dough, cereal products, porridge, gruel, muesli, granola, powdered cereal based product, pasta, semi product, soups, bake-off products, plain bread, and stewed fruit, wherein said food product contains a viable *Lactobacillus* strain according to claim 1.

3. Isolated microorganisms of the *Lactobacillus* strain chosen from the species *Lactobacillus plantarum* LB3e and *Lactobacillus plantarum* LB7c which have been deposited at Deutsche Sammlung von Mikroorganismen and Zeelkulturen, and have been assigned accession number 17852 and 17853 respectively.

* * * * *